United States Patent [19]
Onodera et al.

[11] Patent Number: 6,147,243
[45] Date of Patent: Nov. 14, 2000

[54] METHOD FOR PREPARING ORGANOSILICON COMPOUNDS

[75] Inventors: Satoshi Onodera; Makoto Yoshitake, both of Chiba Prefecture, Japan

[73] Assignee: Dow Corning Toray Silicone Co., Ltd., Tokyo, Japan

[21] Appl. No.: 09/447,870

[22] Filed: Nov. 23, 1999

[30] Foreign Application Priority Data

Jan. 27, 1999 [JP] Japan ................................. 11-018704

[51] Int. Cl.[7] ....................................................... C07F 7/08
[52] U.S. Cl. ................................................................ 556/451
[58] Field of Search ............................................. 556/451

[56] References Cited

U.S. PATENT DOCUMENTS 5,097,054  3/1992  Yamamoto et al. ..................... 556/451
5,493,040  2/1996  Cobb et al. ............................. 556/451

*Primary Examiner*—Paul F. Shaver
*Attorney, Agent, or Firm*—Robert L. McKellar

[57] ABSTRACT

A method for preparing organosilicon compounds comprises: 1) converting the Si-bonded alkoxy in an Si-bonded alkoxy-functional organosilicon compound to the diorganosilyl group by reacting the Si-bonded alkoxy-functional organosilicon compound with organodisiloxane with the general formula $HR_2Si-O-SiR_2H$, where R is a monovalent hydrocarbyl group of 1 to 10 carbon atoms, in alcohol-containing acidic aqueous solution; and subsequently 2) treating with a sulfonic acid catalyst and carboxylic acid. This method is able to convert all the alkoxy groups in the alkoxy-functional organosilicon compound to diorganosilyl. This method can be used to synthesize a high-purity carbosiloxane dendrimer having a narrow molecular weight distribution.

18 Claims, 4 Drawing Sheets

METHOD FOR PREPARING ORGANOSILICON COMPOUNDS

FIELD OF THE INVENTION

This invention relates to a method for the preparation of organosilicon compounds. More particularly, this invention relates to a method for preparing organosilicon compounds that can convert the Si-bonded alkoxy group in organosilicon compounds to the diorganosilyl group at high conversion ratios. The invention additionally relates to a method for synthesizing carbosiloxane dendrimers using said preparative method.

BACKGROUND OF THE INVENTION

Methods are already known for converting the Si-bonded alkoxy in organosilicon compounds to the dimethylsilyl group —O—Si(CH$_3$)$_2$H using 1,1,3,3-tetramethyldisiloxane H(CH$_3$)$_2$Si—O—Si(CH$_3$)$_2$H. Thus, Japanese Laid Open (Kokai) Patent Application Number Hei 4-323222 teaches the reaction of alkoxysilane and 1,1,3,3-tetramethyldisiloxane in aqueous hydrochloric acid solution. Japanese Patent Application Hei 10-29297 (29,297/1998) teaches the reaction of alkoxysilane and 1,1,3,3-tetramethyldisiloxane in the presence of a carboxylic acid and a perfluoroalkanesulfonic acid. The former method suffers from a low conversion in the dimethylsilylation reaction, resulting in the presence of a fair amount of residual alkoxy in the organosilicon compound product. The latter method does provide a high conversion in the dimethylsilylation reaction, but cannot give the target product in high yields due to the occurrence of secondary reactions. These methods have thus been unable to produce SiH-functional organosilicon compounds in high purities from Si-bonded alkoxy-functional organosilicon compounds.

An object of the invention is to provide a method for preparing organosilicon compounds that can convert the Si-bonded alkoxy group to the diorganosilyl group at high conversion ratios and that can do so without the occurrence of secondary reactions. Another object of the invention is to provide a method for preparing a high-purity carbosiloxane dendrimer with a narrow molecular weight distribution through the use of the preceding method.

SUMMARY OF THE INVENTION

This invention relates to a method for preparing organosilicon compounds. Said method is characterized by converting the Si-bonded alkoxy in an Si-bonded alkoxy-functional organosilicon compound to a diorganosilyl group by reacting the Si-bonded alkoxy-functional organosilicon compound with an organodisiloxane having Si-bonded hydrogen atoms in an alcohol-containing acidic aqueous solution and subsequently treating with a sulfonic acid catalyst and carboxylic acid.

DETAILED DESCRIPTION OF THE INVENTION

This invention relates to a method for preparing organosilicon compounds. Said method is characterized by converting the Si-bonded alkoxy in an Si-bonded alkoxy-functional organosilicon compound to the diorganosilyl group with the general formula —O—SiR$^1_2$H (R$^1$=C$_1$ to C$_{10}$ monovalent hydrocarbyl) by reacting the Si-bonded alkoxy-functional organosilicon compound with an organodisiloxane with the general formula HR$^1_2$Si—O—SiR$^1_2$H (R$^1$=C$_1$ to C$_{10}$ monovalent hydrocarbyl) in alcohol-containing acidic aqueous solution and subsequently treating with a sulfonic acid catalyst and carboxylic acid.

The Si-bonded alkoxy-functional organosilicon compound is exemplified by alkoxysilanes, organoalkoxysilanes, alkoxy-functional organosiloxane oligomers, alkoxy-functional organopolysiloxanes, and alkoxy-functional carbosiloxane dendrimers. The alkoxy group is exemplified by methoxy, ethoxy, propoxy, and butoxy, among which methoxy and ethoxy are preferred.

The alkoxysilanes are exemplified by tetraalkoxysilanes such as tetramethoxysilane and tetraethoxysilane; organotrialkoxysilanes such as trimethoxysilane, triethoxy si lane, methyltrimethoxysilane, methyltriethoxy si lane, vinyltrimethoxysilane, phenyltrimethoxysilane, 3-methacryloxypropyltrimethoxysilane, and 3-mercaptopropyltrimethoxysilane; diorganodialkoxysilanes such as dimethyldimethoxysilane, dimethyldiethoxysilane, vinylmethyldimethoxysilane, phenylmethyldimethoxysilane, 3-methacryloxypropylmethyldimethoxysilane, and 3-mercaptopropylmethyldimethoxysilane; and organomonoalkoxysilanes such as trimethylmethoxysilane, trimethylethoxysilane, 3-methacryloxypropyldimethylmethoxysilane, and 3-mercaptopropyldimethylmethoxysilane.

The alkoxy-functional organosiloxane oligomers are exemplified by the partial hydrolysis and condensation products of the above alkoxysilanes and also by 1-methoxy-1,1,3,3,5,5,7,7-octamethyltetrasiloxane, 1-methoxynonamethyltetrasiloxane, and 1-ethoxy-7-vinyloctamethyltetrasiloxane.

The carbosiloxane dendrimer encompassed by this invention is a polymer with a highly branched structure in which the siloxane bond and silalkylene bond alternate and in which the core is a siloxane unit with the general formula X$^1$R$^3_a$SiO$_{(3-a)/2}$. R$^3$ is a monovalent organic group, for example, C$_1$ to C$_{10}$ alkyl, aryl, haloalkyl, ether-containing groups, and ester-containing groups. The subscript a is an integer from 0 to 2. X$^1$ is the silylalkyl group with the following formula at i=1

(R$^4$ is C$_2$ to C$_{10}$ alkylene, R$^5$ is C$_1$ to C$_{10}$ alkyl, R$^6$ is C$_1$ to C$_{10}$ monovalent hydrocarbyl, X$^{i+1}$ is the above-defined silylalkyl group, i is an integer with a value from 1 to 10 that specifies the generation of said silylalkyl group, and b$^i$ is an integer from 1 to 3 wherein b$^i$ in the highest generation is 3).

This alkoxy-functional carbosiloxane dendrimer is exemplified by polymers with the following average molecular formulas.

The alkoxy-functional carbosiloxane dendrimer can be synthesized by an addition reaction between an SiH-functional organosilicon compound and an alkenyltrialkoxysilane in the presence of a platinum transition metal catalyst. The SiH-functional organosilicon compound is exemplified by the compounds having the following average molecular formulas.

wherein $R^1$ represents $C_1$ to $C_{10}$ monovalent hydrocarbyl, $R^2$ represents monovalent organic groups, the subscripts have the following values: l is an integer from 0 to 3, m is an integer with a value of at least 3, n is an integer with a value of at least 0, p is an integer with a value of at least 2, and q and r are both integers with values of at least 4.

The monovalent hydrocarbyl $R^1$ is exemplified by alkyl such as methyl, ethyl, and propyl; alkenyl such as vinyl, allyl, butenyl, and hexenyl; aryl such as phenyl, tolyl, and xylyl; and aralkyl such as benzyl and phenethyl. Methyl is preferred for $R^1$. The monovalent organic group $R^2$ is exemplified by $C_1$ to $C_{10}$ alkyl, aryl, haloalkyl, ether-containing groups, and ester-containing groups.

The alkenyltrialkoxysilane is exemplified by the general formula $R^7Si(OR^5)_3$, in which $R^5$ represents $C_1$ to $C_{10}$ alkyl and $R^7$ represents $C_2$ to $C_{10}$ alkenyl.

The platinum transition metal catalyst is exemplified by chloroplatinic acid, alcohol-modified chloroplatinic acid, olefin complexes of platinum, and platinum/diketonate complexes.

$R^1$ in the organodisiloxane $HR^1{}_2Si—O—SiR^1{}_2H$ represents $C_1$ to $C_{10}$ monovalent hydrocarbyl, for example, alkyl such as methyl, ethyl, and propyl; alkenyl such as vinyl, allyl, butenyl, and hexenyl; aryl such as phenyl, tolyl, and xylyl; and aralkyl such as benzyl and phenethyl. Methyl is preferred for $R^1$.

The alcohol-containing acidic aqueous solution preferably the 2:1:2 (weight) mixture of alcohol:acid:water. The alcohol is exemplified by methanol, ethanol, n-propanol, and isopropanol. The acid is exemplified by concentrated hydrochloric acid, sulfuric acid, carboxylic acids, and sulfonic acids.

The carboxylic acid is exemplified by formic acid, acetic acid, propionic acid, benzoic acid, and substituted benzoic acids. Formic acid and acetic are preferred for their ability to provide a good acceleration of the diorganosilylation reaction.

The sulfonic acid catalyst is a catalyst that accelerates the diorganosilylation reaction. Examples of this component are sulfuric acid and perfluoroalkanesulfonic acids such as trifluoromethanesulfonic acid.

The preparative method of this invention commences with the diorganosilylation in alcohol-containing acidic aqueous solution of the Si-bonded alkoxy by the organodisiloxane $HR^1{}_2Si—O—SiR^1{}_2H$. More specifically, a liquid mixture is prepared from the alcohol-containing acidic aqueous solution and the organodisiloxane using the latter in an amount corresponding to at least 1.0 equivalent and preferably at least 1.2 equivalents with reference to the alkoxy in the Si-bonded alkoxy-functional organosilicon compound. The Si-bonded alkoxy-functional organosilicon compound is then added dropwise to this liquid mixture at from 0 to 80° C., preferably 10 to 50° C., and more preferably 20 to 40° C., to effect conversion of the alkoxy to diorganosilyl. However, since residual alkoxy will still be present in the organosilicon compound afforded by this reaction, after completion of this reaction a sulfonic acid catalyst and carboxylic acid are added to the organosilicon compound product, and the residual alkoxy is converted to diorganosilyl at from 0 to 80° C., preferably 40 to 70° C., and more preferably 45 to 55° C. The carboxylic acid will be used in this stage generally in an amount corresponding to at least 0.6 equivalent and preferably in an amount corresponding to at least 1.0 equivalent with reference to the alkoxy present in the Si-bonded alkoxy-functional organosilicon compound prior to the reaction. The addition of the sulfonic acid catalyst should be at least 200 ppm with reference to the reaction mixture and is preferably at least 500 ppm and more preferably at least 1,000 ppm. A water removal operation may be run between the two stages of this diorganosilylation reaction. After completion of the reaction, work up by a water wash, neutralization, drying, and concentration under reduced pressure will produce a very pure organosilicon compound in which the alkoxy groups previously present in the molecule have all been converted to diorganosilyl.

The preparative method of the invention can be used to synthesize a highly branched carbosiloxane dendrimer in which the siloxane bond and silalkylene bond occur in alternation. This is accomplished through the repetitive and alternating execution of (A) a process in which the Si-bonded alkoxy-functional organosilicon compound is synthesized by an addition reaction between an SiH-functional organosilicon compound and alkenyltrialkoxysilane in the presence of a platinum transition metal catalyst, and (B) a process (diorganosilylation reaction) in which the SiH-functional organosilicon compound is synthesized by reacting the Si-bonded alkoxy-functional organosilicon compound afforded by process (A) with organodisiloxane with the general formula $HR^1{}_2Si—O—SiR^1{}_2H$ ($R^1$ is defined as above) in alcohol-containing acidic aqueous solution followed by treating the reaction product with a sulfonic acid catalyst and carboxylic acid.

A specific example of this reaction sequence is shown below.

One advantage offered by the preparative method described above is that it produces a high-purity SiH-functional organosilicon compound. This advantage accrues because the method can convert all the Si-bonded alkoxy in the molecule to diorganosilyl and can do so without the occurrence of secondary reactions such as, for example, siloxane bond rearrangement. The preparative method of this invention is extremely effective when the starting Si-bonded alkoxy-functional organosilicon compound has been synthesized using a platinum transition metal catalyst. In specific terms, the SiH-functional organosilicon compound afforded by this preparative method is not subject to dehydrogenation of its Si-bonded hydrogen by the platinum transition metal catalyst. Furthermore, the combination of the diorganosilylation reaction of this invention with an addition reaction with alkenyltrialkoxysilane can produce a high-purity carbosiloxane dendrimer with a narrow molecular weight distribution whose molecular weight, determined on a polystyrene basis, has a dispersity index (the ratio Mw/Mn between the weight-average molecular weight Mw and the number-average molecular weight Mn) no greater than 2.

EXAMPLES

In the examples, Me indicates the methyl group. The carbosiloxane dendrimers were identified by $^{29}$Si-nuclear magnetic resonance analysis and gel permeation chromatography (solvent: toluene).

Reference Example 1

107.9 g vinyltrimethoxysilane and 0.02 g 3% isopropanolic chloroplatinic acid solution were introduced into a 300-mL four-neck flask equipped with a stirrer, thermometer, reflux condenser, and addition funnel and were heated to 100° C. while stirring. 80.0 g tetrakis (dimethylsiloxy)silane was then slowly added dropwise from the addition funnel so as to maintain the reaction temperature at 100° C. After the completion of addition, the reaction solution was heated for an additional 1 hour at 120° C. Cooling and concentration under reduced pressure gave 166.9 g of a very light brown liquid.

Analysis of this liquid confirmed it to be carbosiloxane dendrimer with the following formula.

Example 1

235.4 g 1,1,3,3-tetramethyldisiloxane, 74 mL concentrated hydrochloric acid, 148 mL water, and 148 mL isopropanol were introduced into a 1,000-mL four-neck flask equipped with a stirrer, thermometer, reflux condenser, and addition funnel and were stirred. 222.6 g of the carbosiloxane dendrimer synthesized in Reference Example 1 was then added dropwise from the addition funnel over 1 hour at 25 to 30° C. The reaction solution was stirred for an additional 1 hour after the completion of addition.

The reaction solution was subsequently transferred to a separatory funnel, the lower layer was separated off, and the remaining upper layer was washed 3 times with 200 mL water and dried over calcium chloride. After filtration of the resulting solids. 210 g acetic acid and 0.86 mg trifluoromethanesulfonic acid were added and the temperature was raised to 50° C. and a reaction was carried out for 1 hour.

After completion of the reaction, the reaction solution was transferred to a separatory funnel. This was followed by separating off the lower layer, washing 3 times with 200 mL water and once with 200 mL saturated aqueous sodium carbonate solution, and drying over calcium chloride. The resulting solids were filtered off and the reaction solution was then concentrated under reduced pressure to give 342.4 g of a colorless and transparent liquid.

Figure 1:
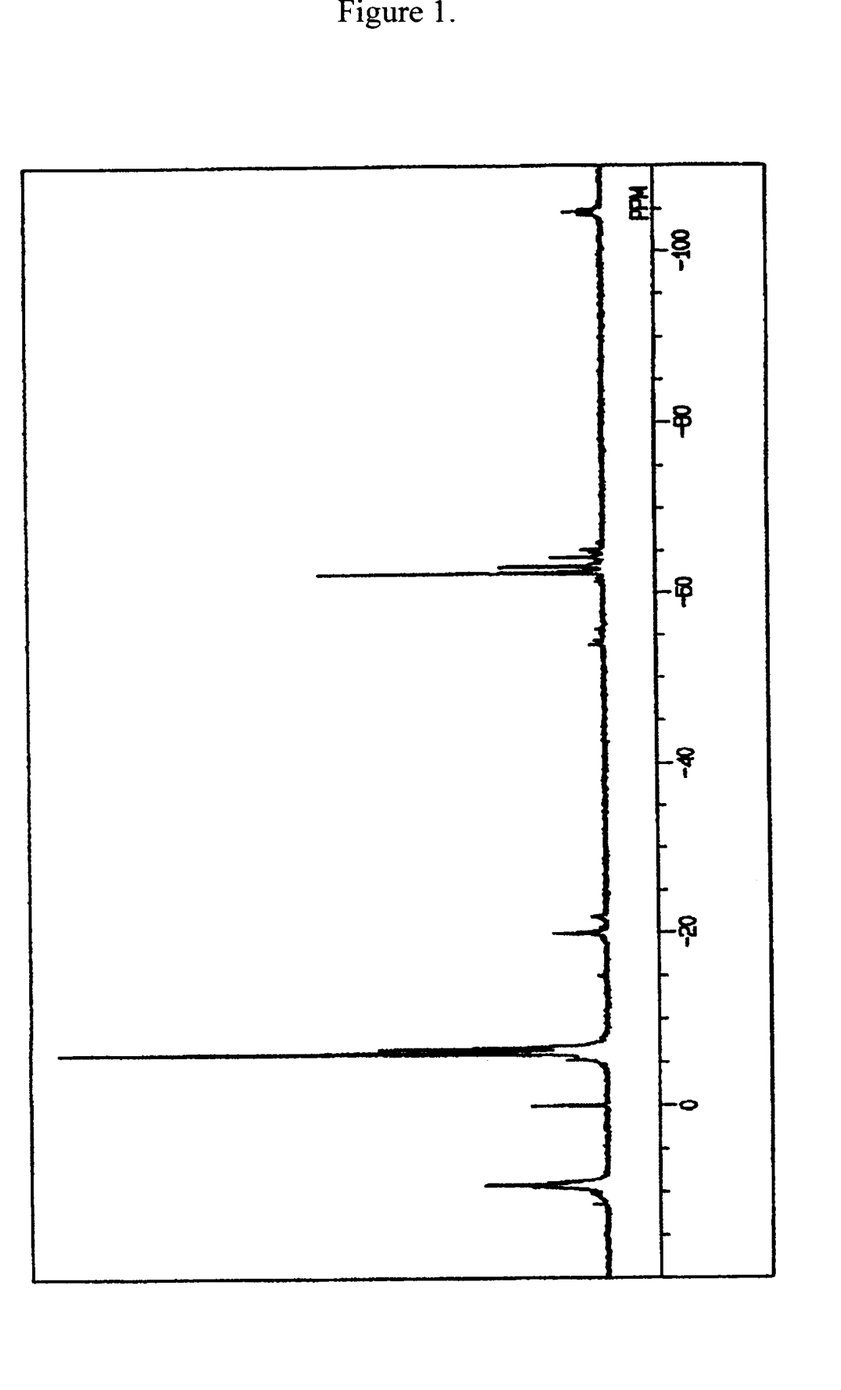
FIG. 1 contains the $^{29}$Si-nuclear magnetic resonance spectrogram of the carbosiloxane dendrimer synthesized in Example 1.

Analysis of this liquid by $^{29}$Si-nuclear magnetic resonance confirmed it to be carbosiloxane dendrimer having the following average molecular formula and having 12 silicon-bonded hydrogen atoms in the molecule.

The results from gel permeation chromatography on this carbosiloxane dendrimer were a number-average molecular weight (polystyrene basis) of 1,866 and a dispersity index of 1.19.

Comparative Example 1

1,101 g 1,1,3,3-tetramethyldisiloxane, 273 mL concentrated hydrochloric acid, 548 mL water, and 548 mL isopropanol were introduced into a 5,000-mL four-neck flask equipped with a stirrer, thermometer, reflux condenser, and addition funnel and were stirred. 842 g of the carbosiloxane dendrimer synthesized in Reference Example 1 was then added dropwise from the addition funnel over 1 hour. The reaction solution was stirred for an additional 1 hour after the completion of addition.

The reaction solution was subsequently transferred to a separatory funnel, the lower layer was separated off, and the remaining upper layer was washed 3 times with 500 mL water and once with 500 mL saturated aqueous sodium carbonate solution and was dried over calcium chloride. Filtration of the resulting solids and concentration of the reaction solution under reduced pressure then gave 1,085 g of a colorless and transparent liquid.

Figure 2:
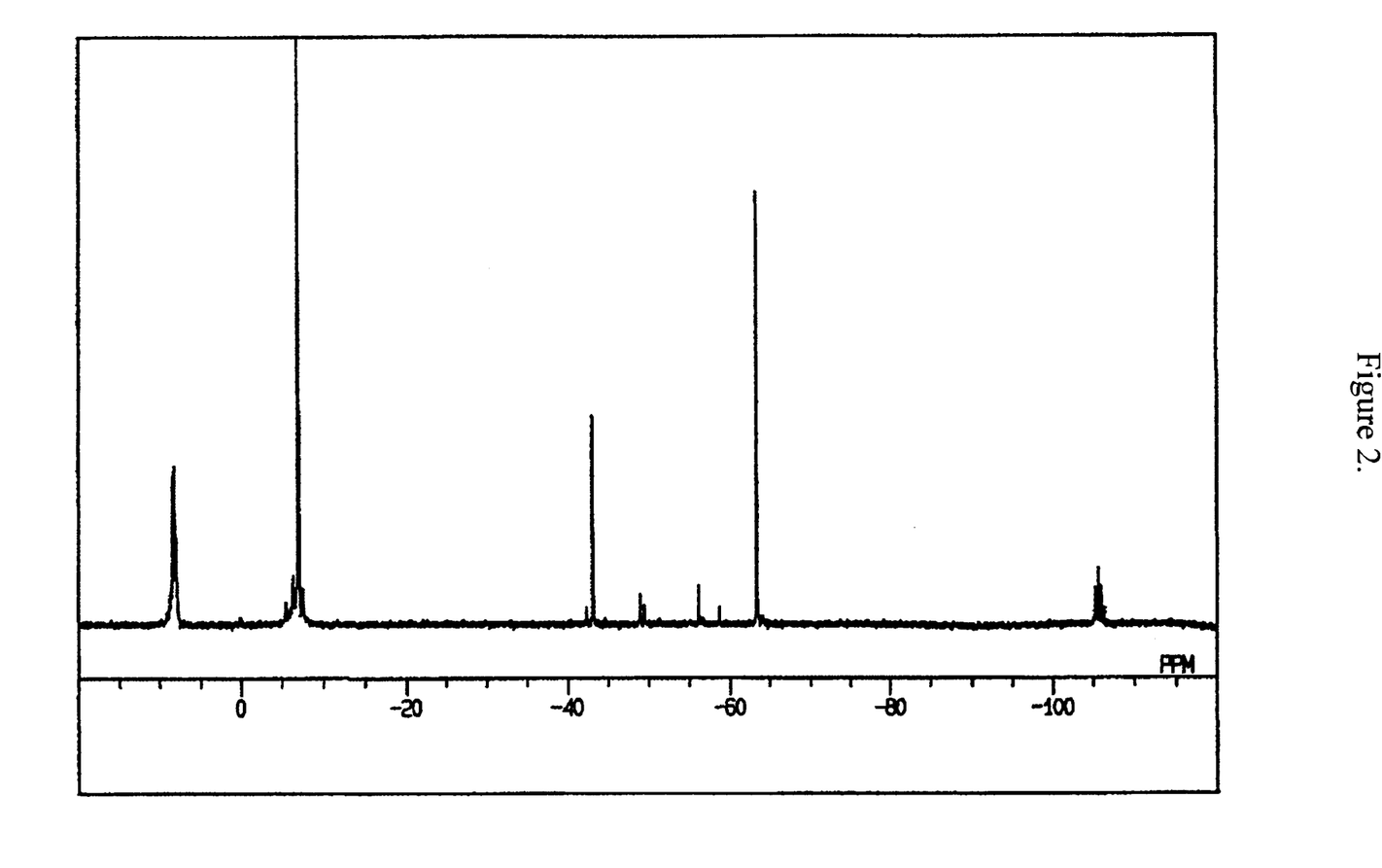
FIG. 2 contains the $^{29}$Si-nuclear magnetic resonance spectrogram of the carbosiloxane dendrimer synthesized in Comparative Example 1.

Analysis of this liquid by 29Si-nuclear magnetic resonance confirmed it to be carbosiloxane dendrimer having the following average molecular formula and having 6.9 silicon-bonded hydrogen atoms in the molecule.

The results from gel permeation chromatography on this carbosiloxane dendrimer were a number-average molecular weight (polystyrene basis) of 1,820 and a dispersity index of 1.07.

Comparative Example 2

140 g 1,1,3,3-tetramethyldisiloxane, 75.2 g acetic acid, and 150 mg trifluoromethanesulfonic acid were introduced into a 200-mL four-neck flask equipped with a stirrer, thermometer, reflux condenser, and addition funnel and were heated to 50° C. 80 g of the carbosiloxane dendrimer synthesized in Reference Example 1 was then added dropwise from the addition funnel and a reaction was carried out for 3 hours.

After completion of the reaction, the reaction solution was transferred to a separatory funnel, the lower layer was separated off, and the remaining upper layer was washed 3 times with 20 mL water and once with 20 ml saturated aqueous sodium carbonate solution and was dried over calcium chloride. Filtration of the resulting solids and concentration of the reaction solution under reduced pressure then gave 109 g of a colorless and transparent liquid.

Figure 3:
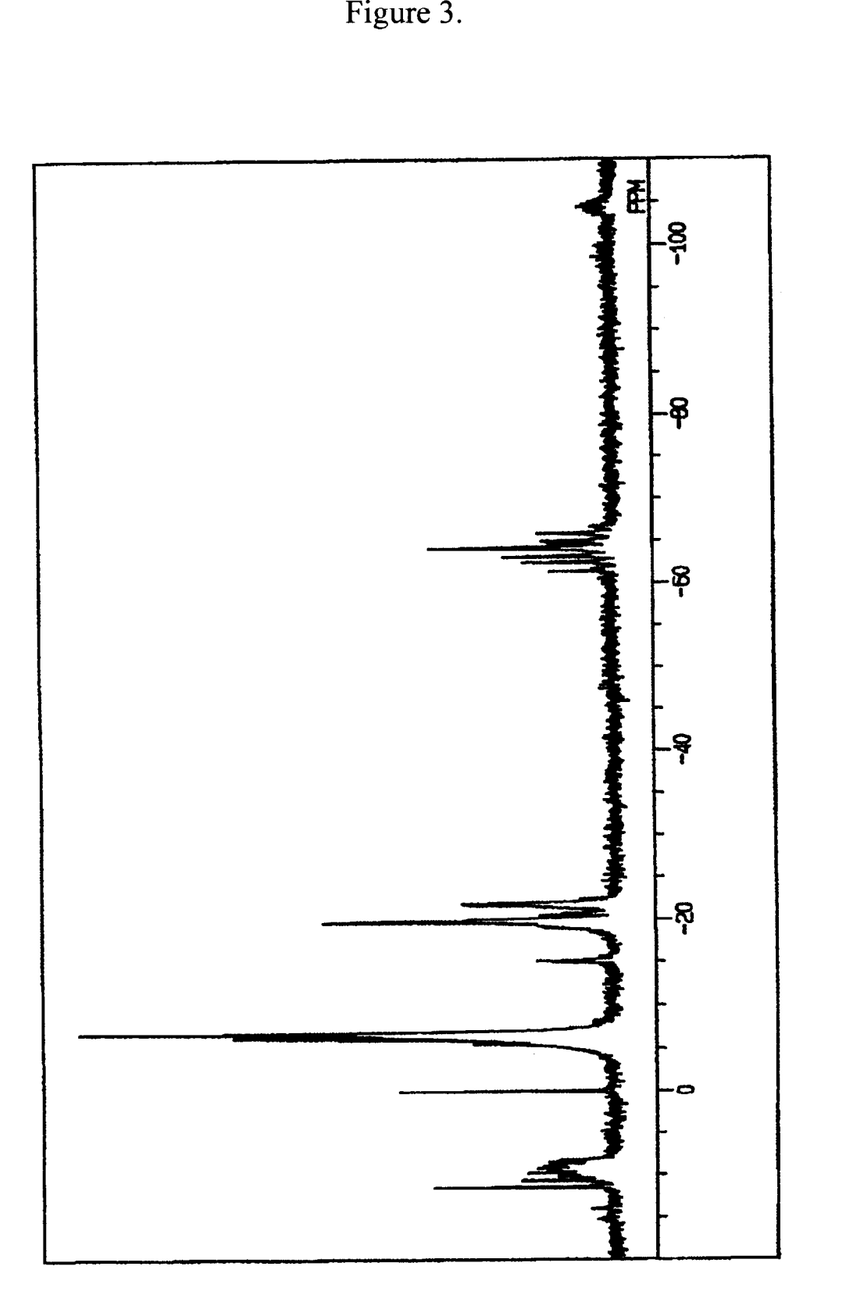
FIG. 3 contains the $^{29}$Si-nuclear magnetic resonance spectrogram of the organosilicon compound synthesized in Comparative Example 2.

Analysis of this liquid by 29Si-nuclear magnetic resonance confirmed it to be an organosilicon compound containing an average of 11 silicon-bonded hydrogen atoms in the molecule. However, the results from $^{29}$Si-nuclear magnetic resonance analysis also indicated that this liquid contained the difunctional siloxane unit (D unit) $(Me)_2SiO_{2/2}$.

Moreover, when this liquid was analyzed by gel permeation chromatography, its molecular weight distribution did not present a single, monodisperse peak, but rather was divided into a number of peaks. Overall, these results indicated that the reaction product contained by-products and that the target carbosiloxane dendrimer with the average molecular formula had not been obtained in high purity. According to gel permeation chromatography this organosilicon compound had a number-average molecular weight (polystyrene basis) of 920 and a dispersity index of 1.84.

Example 2

123.2 g 1,1,3,3-tetramethyldisiloxane, 33 mL concentrated hydrochloric acid, 66 mL water, and 66 mL isopropanol were introduced into a 300-mL four-neck flask equipped with a stirrer, thermometer, reflux condenser, and addition funnel and were stirred. 100.0 g 3-mercaptopropyltrimethoxysilane was then added dropwise at 25 to 30° C. from the addition funnel over I hour. The reaction was stirred for an additional 1 hour after the completion of addition.

The reaction solution was then transferred to a separatory funnel and the lower layer was separated off. The remaining upper layer was washed 3 times with 30 mL water and dried over calcium chloride. After filtering off the resulting solids, 110.1 g acetic acid was added, the temperature was raised to 50° C., and 66.7 mg trifluoromethanesulfonic acid was added. The reaction solution was then reacted for 7 hours.

After completion of the reaction, the reaction solution was transferred to a separatory funnel and the lower layer was separated off followed by washing 3 times with 30 mL water and once with 30 mL saturated aqueous sodium carbonate solution and drying over calcium chloride. Filtering off the resulting solids and concentration of the reaction solution under reduced pressure gave 167.5 g of a colorless and transparent liquid.

Figure 4:
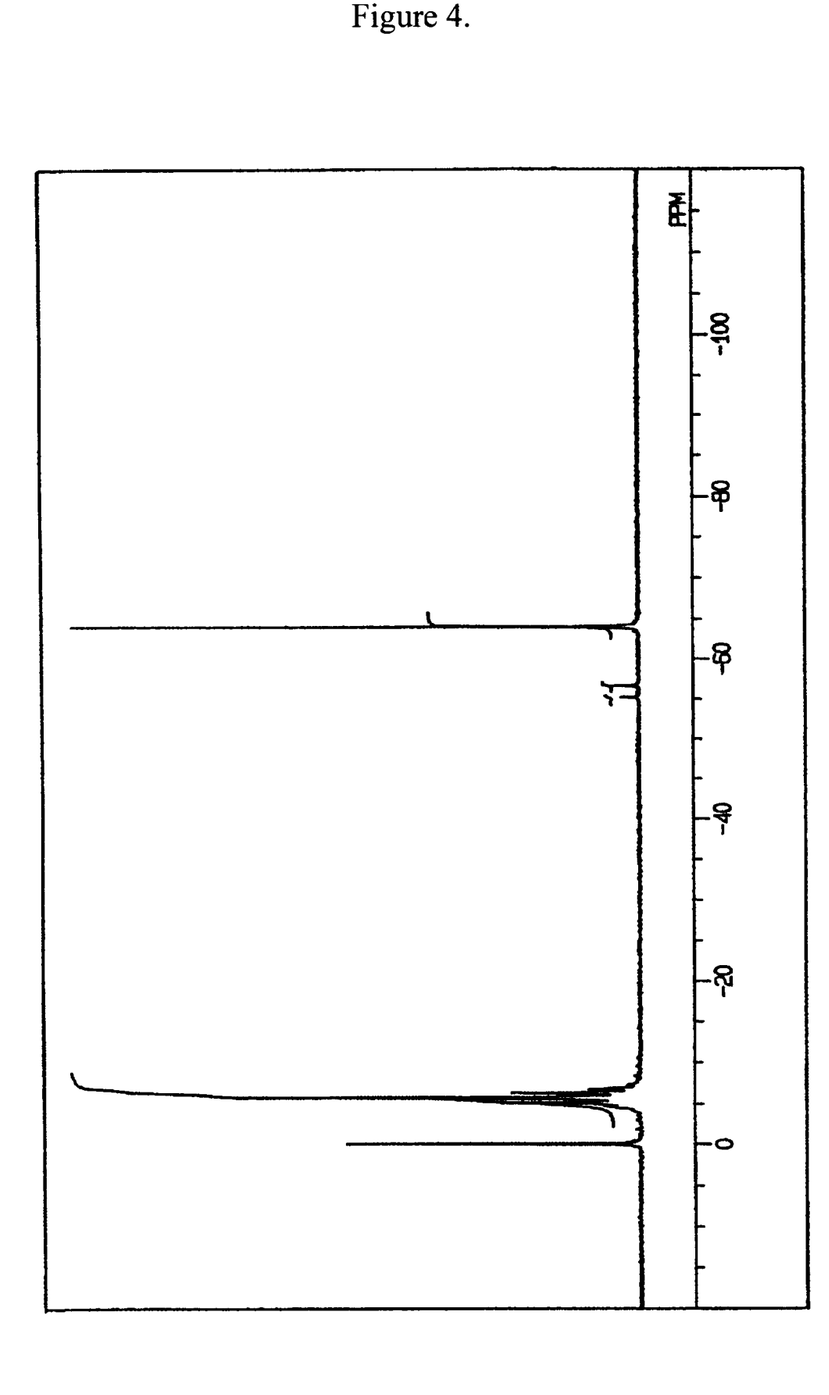
FIG. 4 contains the 29Si-nuclear magnetic resonance spectrogram of the organosilicon compound synthesized in Example 2.

Analysis of this liquid by $^{29}$Si-nuclear magnetic resonance analysis confirmed it to be the organosilicon compound having the following average molecular formula and containing an average of 3 silicon-bonded hydrogen atoms in the molecule.

According to gel permeation chromatography, this organosilicon compound had a number-average molecular weight (polystyrene basis) of 424 and a dispersity index of 1.02.

We claim:
1. A method for preparing organosilicon compounds, wherein the method comprises:
   1) reacting a composition comprising
      i) a Si-bonded alkoxy-functional organosilicon compound,
      ii) an organodisiloxane having the general formula $HR^1_2Si—O—SiR^1_2H$, wherein $R^1$ is a $C_1$ to $C_{10}$ monovalent hydrocarbyl group, and
      iii) an alcohol-containing acidic aqueous solution; and subsequently
   2) treating the product of step 1) with a sulfonic acid catalyst and carboxylic acid.

2. The method of claim 1, wherein step 1) is carried out by heating from 0 to 80° C.

3. The method of claim 2, wherein step 1) is carried out by heating from 10 to 50° C.

4. The method of claim 3, wherein step 1) is carried out by heating from 20 to 40° C.

5. The method of claim 1, wherein the alcohol-containing acidic aqueous solution comprises a mixture of an alcohol selected from the group consisting of methanol, ethanol, n-propanol, and isopropanol; an acid selected from the group consisting of concentrated hydrochloric acid, sulfuric acids, carboxylic acids, and sulfonic acids; and water.

6. The method of claim 5, wherein the alcohol, acid, and water are present in amounts such that an alcohol:acid:water weight ratio is 2:1:2.

7. The method of claim 1, wherein step 2) is carried out by heating to 0 to 80° C.

8. The method of claim 7, wherein step 2) is carried out by heating to 40 to 70° C.

9. The method of claim 8, wherein step 2) is carried out by heating to 45 to 55° C.

10. The method of claim 1, wherein the carboxylic acid is selected from the group consisting of formic acid, acetic acid, propionic acid, benzoic acid, and substituted benzoic acids.

11. The method of claim 1, wherein the sulfonic acid catalyst is selected from the group consisting of sulfuric acid and perfluoroalkanesulfonic acids.

12. The method of claim 1, wherein the Si-bonded alkoxy-functional organosilicon compound is selected from the group consisting of alkoxysilanes, organoalkoxysilanes, alkoxy-functional organosiloxane oligomers, alkoxy-functional organopolysiloxanes, and alkoxy-functional carbosiloxane dendrimers.

13. The method of claim 12, wherein the alkoxy-functional carbosiloxane dendrimer is a polymer comprising a siloxane unit having the general formula $X^1R^3_aSiO_{(3-a)/2}$, wherein $R^3$ is a monovalent organic group, a is an integer from 0 to 2, $X^1$ is a silylalkyl group with the following formula at i=1 wherein $R^4$ is $C_2$ to $C_{10}$ alkylene, $R^5$ is $C_1$ to $C_{10}$ alkyl, $R^6$ is $C_1$ to $C_{10}$ monovalent hydrocarbyl, $X^{i+1}$ is the silylalkyl group, i is an integer with a value from 1 to 10, and $b^i$ is an integer from 1 to 3.

14. The method of claim 1, wherein the Si-bonded alkoxy-functional organosilicon compound is prepared by an addition reaction between an SiH-functional organosilicon compound and an alkenyltrialkoxysilane in the presence of a platinum transition metal catalyst.

15. The method of claim 14, wherein the Si-bonded alkoxy-functional organosilicon compound is an alkoxy-functional carbosiloxane dendrimer.

16. A method for preparing a carbosiloxane dendrimer, wherein the method comprises:
   1) repetitive and alternating execution of processes (A) and (B), wherein
      process (A) comprises synthesizing an Si-bonded alkoxy-functional organosilicon compound by an addition reaction between an SiH-functional organosilicon compound and alkenyltrialkoxysilane in the presence of a platinum transition metal catalyst, and
      process (B) comprises converting the Si-bonded alkoxy in the Si-bonded alkoxy-functional organosilicon compound afforded by process (A) to a diorganosilyl group having the formula $—O—SiR^1_2H(R^1=C_1$ to $C_{10}$ monovalent hydrocarbyl) by reacting said Si-bonded alkoxy-functional organosilicon compound with organodisiloxane with the general formula $HR^1_2Si—O—SiR^1_2H$ ($R^1=C_1$ to $C_{10}$ monovalent hydrocarbyl) in alcohol-containing acidic aqueous solution; and subsequently
   2) treating the product of step 1) with a sulfonic acid catalyst and carboxylic acid.

17. The method of claim 16 wherein the SiH-functional organosilicon compound is selected from the group consisting of compounds with the following average molecular formulas:

wherein $R^1$ is a $C_1$ to $C_{10}$ monovalent hydrocarbyl, $R^2$ is a monovalent organic group, l is an integer from 0 to 3, m is an integer with a value of at least 3, n is an integer with a value of at least 0, p is an integer with a value of at least 2, q is an integer with a value of at least 4, and r is an integer with a value of at least 4.

18. The method of claim 16, wherein the alkenyltrialkoxysilane has the general formula $R^7Si(OR^5)_3$, wherein $R^5$ represents $C_1$ to $C_{10}$ alkyl and $R^7$ represents $C_2$ to $C_{10}$ alkenyl.

* * * * *